(12) United States Patent
Giovannoli

(10) Patent No.: US 8,545,489 B2
(45) Date of Patent: *Oct. 1, 2013

(54) METHOD AND APPARATUS FOR SKIN REDUCTION

(76) Inventor: Joseph Giovannoli, Park Ridge, NJ (US)

( * ) Notice: Subject to any disclaimer, the term of this patent is extended or adjusted under 35 U.S.C. 154(b) by 997 days.

This patent is subject to a terminal disclaimer.

(21) Appl. No.: 11/485,752

(22) Filed: Jul. 13, 2006

(65) Prior Publication Data

US 2007/0068537 A1    Mar. 29, 2007

Related U.S. Application Data

(63) Continuation-in-part of application No. 11/175,004, filed on Jul. 5, 2005, which is a continuation-in-part of application No. PCT/US2005/001556, filed on Jan. 21, 2005.

(60) Provisional application No. 60/538,847, filed on Jan. 23, 2004.

(51) Int. Cl.
    *A61B 18/18*    (2006.01)
(52) U.S. Cl.
    USPC .............................. 606/9; 606/167; 128/898
(58) Field of Classification Search
    USPC ............................................. 606/167
    See application file for complete search history.

(56) References Cited

U.S. PATENT DOCUMENTS

| 3,742,954 A | 7/1973 | Strickland |
| 3,911,909 A | 10/1975 | DiMatteo |
| 3,949,741 A | 4/1976 | Hofmann |
| 3,990,451 A * | 11/1976 | Gibbs ........................... 606/174 |
| 4,576,163 A | 3/1986 | Bliss |
| 4,832,045 A | 5/1989 | Goldberger |
| 5,000,752 A * | 3/1991 | Hoskin et al. ...................... 606/9 |
| 5,183,053 A | 2/1993 | Yeh et al. |
| 5,250,026 A | 10/1993 | Ehrlich et al. |
| 5,254,132 A | 10/1993 | Barley et al. |
| 5,370,642 A | 12/1994 | Keller |
| 5,396,881 A | 3/1995 | Klein |
| 5,413,268 A | 5/1995 | Green et al. |
| 5,417,683 A | 5/1995 | Shiao |

(Continued)

OTHER PUBLICATIONS

International Search Report and Written Opinion for corresponding PCT/US05/01556, dated Sep. 14, 2005; 7 pgs.

(Continued)

*Primary Examiner* — Bill Thomson
*Assistant Examiner* — Lynsey Crandall
(74) *Attorney, Agent, or Firm* — Kaplan Breyer Schwarz & Ottesen LLP

(57) ABSTRACT

A method for reducing skin is disclosed, in which a plurality of incisions or removals are made to collectively form a patch of skin to be reduced, instead of making a single large treatment of the patch. Thus, scarring after healing is less noticeable. Preferably, the treated regions of skin are arranged such that a total area of all removed skin segments taken in a direction perpendicular to an axis of said patch changes gradually along said axis. The removed regions of skin are preferably navicular in shape, and the patches are preferably navicular in shape in the event an elongated incision is made. The removal of skin regions can be realized by proper treatment methods such as incisions and laser treatment. The mask may be attached to the patch of skin to be treated after said skin is stretched.

37 Claims, 10 Drawing Sheets

(56) References Cited

U.S. PATENT DOCUMENTS

| | | | |
|---|---|---|---|
| 5,507,765 | A | 4/1996 | Mott |
| 5,643,252 | A | 7/1997 | Waner et al. |
| 5,643,308 | A | 7/1997 | Markman |
| 5,713,375 | A * | 2/1998 | McAllister ............... 128/898 |
| 5,797,926 | A | 8/1998 | Mehl, Sr. |
| 5,810,801 | A * | 9/1998 | Anderson et al. ............. 606/9 |
| 5,922,000 | A | 7/1999 | Chodorow |
| 5,944,596 | A | 8/1999 | Hargrove |
| 6,022,345 | A * | 2/2000 | Miller et al. .................. 606/9 |
| 6,050,990 | A * | 4/2000 | Tankovich et al. ............ 606/9 |
| 6,074,382 | A | 6/2000 | Asah et al. |
| 6,241,753 | B1 | 6/2001 | Knowlton |
| 6,595,934 | B1 | 7/2003 | Hissong et al. |
| 6,660,018 | B2 * | 12/2003 | Lum et al. ................. 606/181 |
| 6,915,804 | B2 | 7/2005 | Melker et al. |
| 6,997,923 | B2 | 2/2006 | Anderson et al. |
| 7,090,670 | B2 * | 8/2006 | Sink ............................. 606/9 |
| 7,744,544 | B2 | 6/2010 | Ward et al. |
| 8,251,915 | B2 | 8/2012 | Dunn |
| 2002/0161357 | A1 * | 10/2002 | Anderson et al. ............. 606/9 |
| 2003/0016654 | A1 | 1/2003 | Das et al. |
| 2003/0181936 | A1 * | 9/2003 | Trautman et al. .......... 606/186 |
| 2003/0216751 | A1 | 11/2003 | Bircoll |
| 2004/0049221 | A1 | 3/2004 | Loshakove et al. |
| 2004/0082940 | A1 * | 4/2004 | Black et al. .................. 606/9 |
| 2004/0087992 | A1 | 5/2004 | Gartstein et al. |
| 2005/0033197 | A1 | 2/2005 | Cottler |
| 2005/0154380 | A1 | 7/2005 | DeBenedictis et al. |
| 2005/0251117 | A1 * | 11/2005 | Anderson et al. ............. 606/9 |
| 2005/0283141 | A1 | 12/2005 | Giovannoli |
| 2006/0020309 | A1 * | 1/2006 | Altshuler et al. ........... 607/88 |
| 2006/0155266 | A1 * | 7/2006 | Manstein et al. ............ 606/17 |
| 2007/0135731 | A1 | 6/2007 | Ward et al. |
| 2007/0270738 | A1 | 11/2007 | Wu et al. |
| 2009/0149775 | A1 | 6/2009 | Lander |

OTHER PUBLICATIONS

International Preliminary Report on Patentability for corresponding PCT/US05/01556, dated Aug. 3, 2006; 5 pgs.

International Preliminary Report on Patentability of International Application PCT/US2007/073459, filed Jul. 13, 2007.

International Search Report and Written Opinion, dated Oct. 24, 2008 of International Application PCT/US2007/073459.

An Office Action, dated Apr. 17, 2009 in U.S. Appl. No. 11/175,004, filed Jul. 5, 2005.

A Final Office Action, dated Jan. 19, 2010 in U.S. Appl. No. 11/175,004, filed Jul. 5, 2005.

An Office Action, dated Aug. 18, 2010 in U.S. Appl. No. 11/175,004, filed Jul. 5, 2005.

An Office Action, dated Mar. 1, 2011 in U.S. Appl. No. 11/175,004, filed Jul. 5, 2005.

An Office Action, dated Aug. 2, 2010 in U.S. Appl. No. 11/490,663, filed Jul. 21, 2006.

A Final Office Action, dated Jan. 25, 2011 in U.S. Appl. No. 11/490,663, filed Jul. 21, 2006.

Nguyen,Vix, "Related U.S. Appl. No. 12/824,836 Office Action", May 11, 2012, Published in: US.

Blaine Copenheaver, "Related International Patent Application PCT/US2006/025983 International Search Report and Written Opinion", Oct. 2, 2007, Publisher: USPTO, Published in: US.

Masashi Honda, "Corresponding International Patent Application PCT/US05/001556 International Preliminary Report on Patentability", Jul. 26, 2006, Publisher: USPTO, Published in: US.

Liptitz, Jeffrey Brian, "Related Application U.S. Appl. No. 11/490,663 Office Action", Nov. 16, 2011, Publisher: USPTO, Published in: US.

Nguyen,Vix, "Related U.S. Appl. No. 12/824,836 Final Office Action", Nov. 21, 2012, Publisher: USPTO, Published in: US.

Shiela H. Veney, "Corresponding International Patent Application PCT/US05/01556 International Search Report and Written Opinion", Sep. 14, 2005, Publisher: USPTO, Published in: US.

Lipitz, Jeffrey Brian, "Related U.S.Appl. No. 11/490,663 Office Action", Apr. 18, 2012, Publisher: USPTO, Published in: US.

Tran et al., "Biopsy of the Pigmented Lesion—When and How", Sep. 1, 2008, Publisher: American Academy of Dermatology, Inc., Published in: US.

Kathy P. An et al., "Surgical Management of Cutaneous Malignancies", 2001, vol. 19, Publisher: Elsevier Science Inc., Published in: US.

Thomas E. Roher, "Planning the Closure", 2003, Publisher: Elsevier Inc., Published in: US.

Orin Goldblum, MD, "Surgical Pearl: The Single-use, Surgical Curette Blade", 2004, vol. 50, No. 2, Publisher: Journal of the American Academy of Dermatology, Published in: US.

James A, Bush et al., "Skin Tension or Skin Compression? Small Circular Woulds are Likely to Shrink, Not Gape", "Journal of Plastic, Reconstructive & Aesthetic Surgery", 2008, vol. 61, Publisher: Elsevier Ltd, Published in: UK.

Lindsay Ann Warino et al., "Surgical Pearl: Removal of Large Oval Lesions With a Small Oval Punch", Sep. 2006, Publisher: Journal of the American Academy of Dermatology, Inc., Published in: US.

Frenkiel et al., "The Elliptical Punch Biopsy: A Simple Technique", Dec. 25, 2008, Publisher: British Association of Plastic, Reconstructive and Aesthetic Surgeons, Published in: AU.

* cited by examiner

METHOD AND APPARATUS FOR SKIN REDUCTION

RELATED APPLICATIONS

This is a continuation-in-part of U.S. patent application Ser. No. 11/175,004, which is a continuation in part of International Application No. PCT/US05/01556 filed on Jan. 21, 2005, which in turn claims benefit of provisional application No. 60/538,847 filed on Jan. 23, 2004. The entirety of these applications is incorporated here by reference.

BACKGROUND OF THE INVENTION

The present invention relates to techniques in the field of surgical instruments and methods for skin reduction or tightening, and more particularly, to a method and apparatus for removing skin with minimal scarring after healing, e.g., in skin reduction surgery and for the removal of skin wrinkles and laxities.

A number of methods have been used to tighten skin for the purpose of restoring a more youthful appearance. Several methods well known in the art are dermabrasion, laser resurfacing and chemical peels. In using these facial resurfacing process, the epidermis is denuded to a certain depth by direct physical, chemical or thermal injury applied to the skin. The cutaneous injury induces a healing response, resulting in the deposition of a new skin matrix with improved appearance. Skin rejuvenation occurs by a proliferation of fibroblast activity, the action of inflammatory mediators, and a deposition of new collagen and other dermal matrix proteins. The object of these methods is to create a smoother and more attractive epidermal layer. Using a different principal, Di Matteo (U.S. Pat. No. 3,911,909) discloses a device that applies pressure to the interior surface of the mouth and the adjacent exterior surface of the face for the purpose of mechanically flattening facial wrinkles. In a method described by Hofmann (U.S. Pat. No. 3,949,741), pressure-sensitive adhesive film is applied to the skin, left for a few hours, and stripped off, removing with it a layer of dead epidermal cells. A number of patents describe various means by which collagen in the skin is caused to contract by heating with lasers or electromagnetic radiation. These processes create collagen scarring below the skin surface, which tightens the skin at the treated site. U.S. Pat. No. 6,241,753 describes a method by using electromagnetic radiation and U.S. Pat. No. 5,370,642 describes a method using laser energy. A noninvasive surgical method for tightening the skin is described in McAllister (U.S. Pat. No. 5,713,375) wherein a skin scratching tool with a plurality of generally parallel cutting blades is applied to the skin. The resulting parallel "scratches" in the skin heal and thereby cause the skin to tighten. Another method involves subcutaneous implanting of gold threads. The threads are implanted in sub-dermal space at the level of the derma inner edge and are aligned along and/or across wrinkles and skin folds. This method is said to induce collagen formation.

Within the category of surgery, it is generally known that plastic surgeons perform face-lifts and other types of rhytidectomies to tighten skin on the face, arms and other parts of the body. In a face-lift procedure, the surgeon begins an incision in the area of the temple hair, just above and in front of the ear, and then continues around the lobe, circling the ear before returning to the point of origin in the scalp. The skin is raised outward before the surgeon repositions and tightens the underlying muscle and connective tissue. Some fat may be removed, as well as excess skin. For men, the incision is aligned to accommodate the natural beard lines. In all cases, the incision is placed where it will fall in a natural crease of the skin for camouflage. One drawback resulting from placing an incision remote from the specific area of laxity is that the surgery stretches more skin than is necessary to reduce skin laxity or to reduce wrinkles. Such stretching reduces skin thickness and limits the number of times such procedures can be repeated. In addition, large scale pulling of the skin toward the hairlines can, in some cases, give the face an artificial look considered by many to be characteristic of apparent or repeated face-lifts. In addition, such procedures do not always resolve wrinkling in the mouth and chin areas. Moreover, such procedures do not lend themselves to resolving problems in other small areas of the body such as wrinkling at the junction of the thumb and forefinger.

In conventional skin treatment surgical practice, surgeons typically use a scalpel to remove skin abnormalities such as lesions or tumors. This is different from diagnostic skin sampling wherein biopsy punches are used to reduce reliance on the personal skill of the medical doctor. Such diagnostic punches are disclosed by Gibbs (U.S. Pat. No. 3,990,451) and Yeh et al. (U.S. Pat. No. 5,183,053). To avoid the unpleasant "dog ears" that may result from a circular or oval-shaped incision, for example, surgeons usually make a navicular-shaped incision (boat-shaped), around the lesion or tumor. However, these skin treatment techniques may not result in a satisfying aesthetic appearance if applied to the practice of cosmetic surgery since a single incision to reduce skin area for removing wrinkles or laxities may result in noticeable scarring after healing.

Therefore, there exists a need for an improved means for performing surgical skin reduction such as in rhytidectomies operations, which addresses the inherent limitations resulting from the need to avoid creating obvious scars and the resulting unfortunate stretching of more skin than would otherwise be involved in skin, laxity and wrinkle reduction.

Thus, it is an object of the present invention to provide a method and device whereby skin reduction is achieved with minimal or barely visible scarring and by treating skin proximate the wrinkle, laxity or reduction area to be treated.

SUMMARY OF THE INVENTION

According to a first aspect of the present invention, a method for reducing skin is provided, which comprises the steps of determining a patch of skin to be treated, and removing a plurality of isolated regions of skin collectively forming the patch of skin. Thus, instead of treating the patch of the skin as a single region, many small regions of skin are treated, e.g., by incisions or resurfacing, which results in less noticeable scarring.

Preferably, the treated regions of skin are arranged such that a total area of all removed skin segments taken in a direction perpendicular to an axis of the patch changes gradually along the patch axis. Preferably, the skin patch formed by the multiple regions of skin has an elliptical or navicular shape. Thus, the closed incisions or removed skin regions collectively pull the skin on either side of the reduced area in a gradual and uniform manner similar to the change in area with position along a navicular incision.

According to a second aspect of the present invention, an apparatus for excising skin is provided, which comprises an array of punches for excising a patch of skin, and the punches are arranged to collectively form an operational region that matches the patch of skin to be treated. Thus, the patch is excised by making plural incisions in the skin, resulting in less obvious scars after healing.

Preferably, the punches are dimensioned and arranged such that a total area of all incised skin segments taken in a direction perpendicular to an axis of the patch changes gradually along the patch axis.

Preferably, the operational region and the matching patch have an elliptical or navicular shape. Preferably, each punch has a cutting edge of navicular shape.

According to a third aspect of the present invention, a punch array for facilitating excision of a patch of skin is provided, which comprises an array of punches each having a cutting edge for cutting a region of the skin within the patch to be treated when the array of punches moves relative to a holder thereof in a direction towards the skin.

Preferably, the holder comprises a housing having a resilient top for driving the punches to move towards the skin when a force is applied to the top.

Preferably, each punch comprises a hollow body inside which an adhesive rod is slidably accommodated and the rod is provided with an adhesive or other gripping means at an end surface for gripping a skin plug incised by the cutting edge.

According to a fourth aspect of the present invention, a method of skin reduction is provided, which comprises steps of removing or resurfacing a plurality of regions of skin with a laser. Preferably, the plurality of regions of skin collectively form a patch of skin to be treated.

Preferably, a mask with a plurality of holes may be provided to cover the skin so that the laser only treats the regions of skin exposed by the holes in the mask. Preferably, The holes are dimensioned and arranged such that a total area of all the treated skin segments taken in a direction perpendicular to an axis of the patch changes gradually along the patch axis.

The laser may comprises a single or multiple wide area beams each for treating one or more of regions exposed by the holes, or a single narrow area beam that is movable to multiple locations each corresponding to one of the plurality of regions of the skin.

In accordance with one embodiment, the mask is adhered to the skin over a defined area, and the regions of the skin to be treated are accessible through the holes in the mask. The mask may be placed on the defined area after stretching the skin and applying adhesive to either the skin or the mask itself, so that the skin is prevented from un-stretching until the mask is removed after the treatment.

With the teaching of the present invention, the incisions can be very small so as to achieve barely visible scarring. Using a precision punch-like apparatus or laser according to the present invention can achieve very small navicular or other shaped incisions. This makes it possible to create precisely shaped incisions as small as a few millimeters in length, which achieve very small hairline scarring that is less noticeable. Although each excision removes very little tissue, an array of incisions can remove significant amounts of tissue. Also, inasmuch as the reduction is placed where it is needed, it is not necessary to remove the quantities of tissue common to a face-lift. This further benefits the patient by avoiding reducing skin thickness in areas unrelated to the intended area to be tightened or reduced.

BRIEF EXPLANATION OF THE DRAWINGS

The above and other features and advantages of the present invention will become clearer after reading the detailed description of the preferred embodiments according to the present invention with reference to the accompanying drawings in which.

DETAILED EXPLANATION OF THE PREFERRED EMBODIMENTS

The present invention will be described in detail below with the preferred embodiments, in which similar reference numbers designate similar elements throughout the drawings.

Figures 1A, 1B:
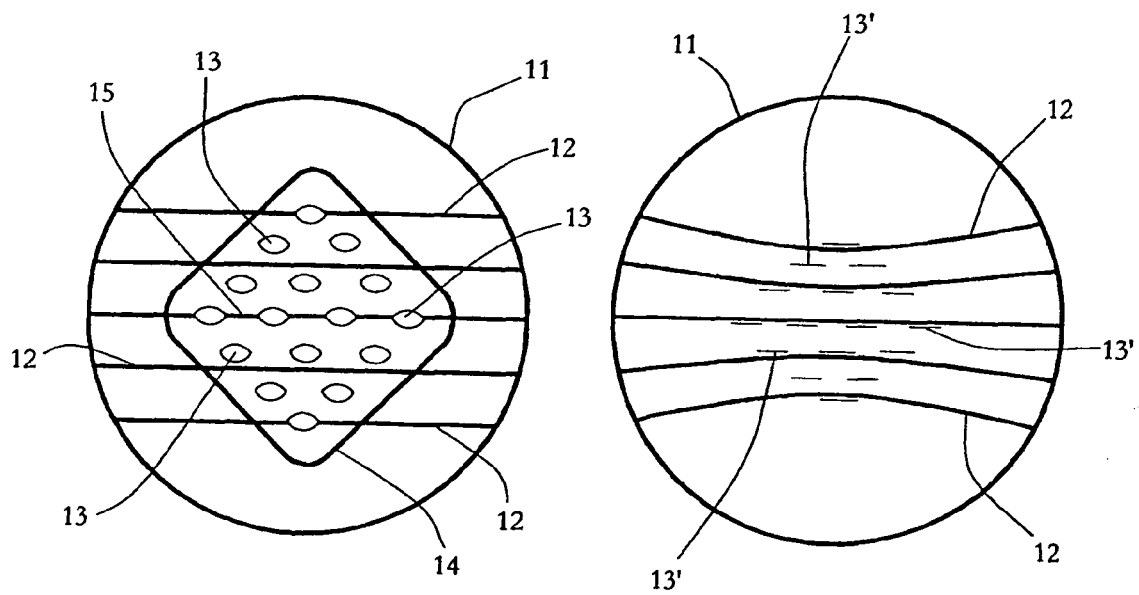
FIGS. 1a and 1b schematically illustrate an embodiment according to the present invention in which a plurality of incisions are made for excising a patch of skin, before and after closure of the incisions respectively.

FIG. 1a is a plan view representation of a circular section 11 of skin with parallel prereduction orientation lines 12 and an array of excised navicular incisions 13 of skin prior to closure. The array of incisions 13 of skin collectively form a patch 14 that is to be tightened or treated. FIG. 1b is a plan view representation of the circular section 11 shown in FIG. 1a after closure of the incisions 13 of skin. The closures of incisions 13 are shown as short lines 13' in FIG. 1b, which are usually unnoticeable when the incisions 13 are very small.

Preferably, according to the teaching of the present invention, the array of incisions 13 are arranged according to an "area rule" wherein the total area of incision segments taken in a direction perpendicular to an axis 15 of the patch 14 changes gradually along the axis 15. It is understood that such gradual changes include incremental increases, stasis (if any) and incremental decreases. Preferably, no discontinuity exists in the change.

Figure 1C:
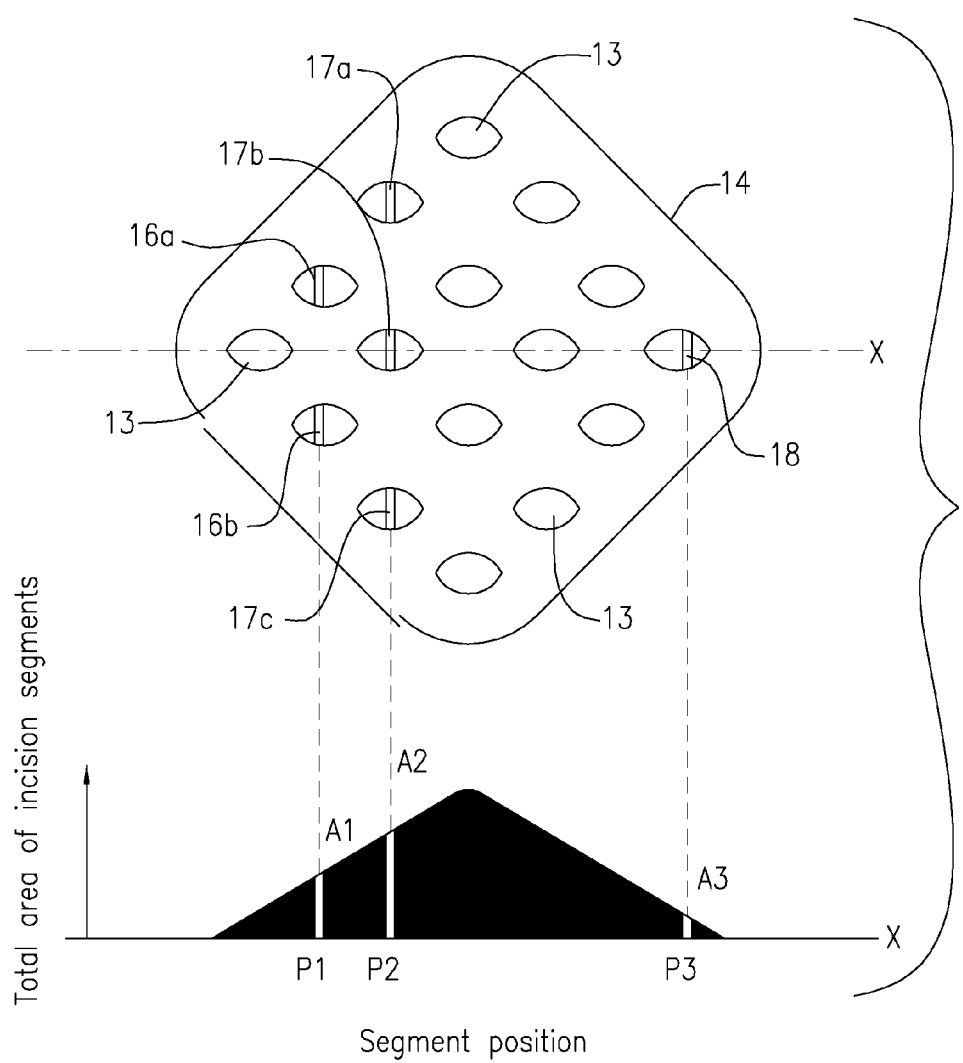
FIG. 1c illustrates that the plurality of navicular incisions in FIGS. 1a and 1b are arranged according to the "area rule" to collectively form a generally diamond-shaped patch of skin to be treated.

The "area rule" is now explained in more detail with reference to FIG. 1c, which is a plan view of the array of incisions shown in FIGS. 1a and 1b with an associated relative area graphical representation that represents a total area of incision segments along an axis "X" of the skin patch 14. The total areas and corresponding incision segments at three positions P1, P2 and P3 along the axis "X" are exemplarily shown. Specifically, total area A1 at position P1 is a sum of areas of incision segments 16a and 16b which are taken at the position P1 in a direction perpendicular to the axis "X". All the segments are considered to have the same width, which is a predetermined length of the axis "X". Similarly, total area A2 is a sum of areas of incision segments 17a, 17b and 17c taken at the position P2, and total area A3 is the area of the incision segment 18 taken at the position P3. According to the "area rule", the total area of the incision segments taken in a direction perpendicular to the axis "X" changes gradually along the axis "X", as illustrated in the area graphical representation in FIG. 1c. In other words, the collective incision area change along the axis "X" of the incision array maintains a gradual and continuous increase, stasis (if any) and decrease in collective incision area perpendicular to the axis "X", preferably without discontinuities in incremental area change. Since all the segments have the same width, the "area rule" may also be interpreted as that the sum of the heights of all the segments corresponding to a point on the axis "X" changes gradually along the axis "X".

Observing this "area rule" when designing surgical incision arrays will provide a continuous and balanced tightening of skin on closing the array incisions, equivalent to having performed one large area rule incision such as in a single elliptical or navicular incision performed by a scalpel or a biopsy punch, but without one large noticeable scar. The closed incisions 13 collectively pull the skin on either side of the axis "X" of the reduced patch in a gradual and uniform manner as if in a single large navicular incision. The scar pattern in FIG. 1b demonstrates this concept.

Preferably, the axis "X" of the skin patch 14 that is to be reduced is oriented parallel to the lines of least skin tension of the skin patch 14, such as lines perpendicular to the long axis of an arm.

The skin patch 14 to be treated or reduced, which is collectively formed by the plurality of incisions 13 arranged following the "area rule", may be of a navicular shape (FIG. 2), an elliptical shape (FIG. 3), a circular shape, a rectangular or elongated shape (such in a scalp reduction) or other proper shapes. The incisions 13 are preferably of navicular shape to avoid "dog ears", and can be either identical (FIG. 2) or different (FIG. 3).

Figure 2:
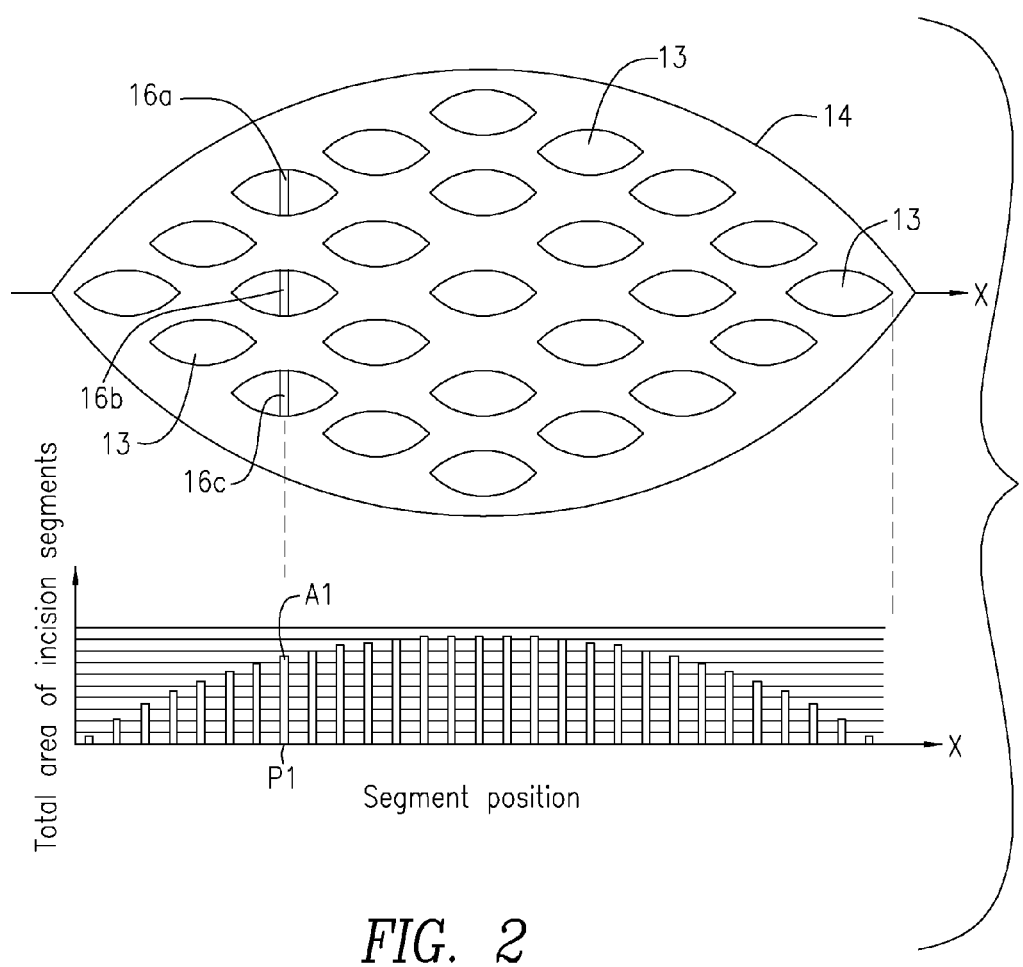
FIG. 2 illustrates another embodiment according to the present invention in which a plurality of navicular incisions are arranged according to the "area rule" to collectively form a navicular patch of skin to be treated.

FIG. 2 illustrates an embodiment in which a navicular skin patch 14 is collectively formed by a plurality of identical navicular incisions 13. The incisions 13 are arranged according to the "area rule" as explained above, and the total area of incision segments gradually increases and decreases along the axis "X" which extends through the two ends of the navicular skin patch 14, as illustrated in the area graphical representation. For example, a total area A1 at position P1 represents the sum of areas of the incision segments 16a, 16b and 16c taken at the position P1 in a direction perpendicular to the axis "X".

Figure 3:
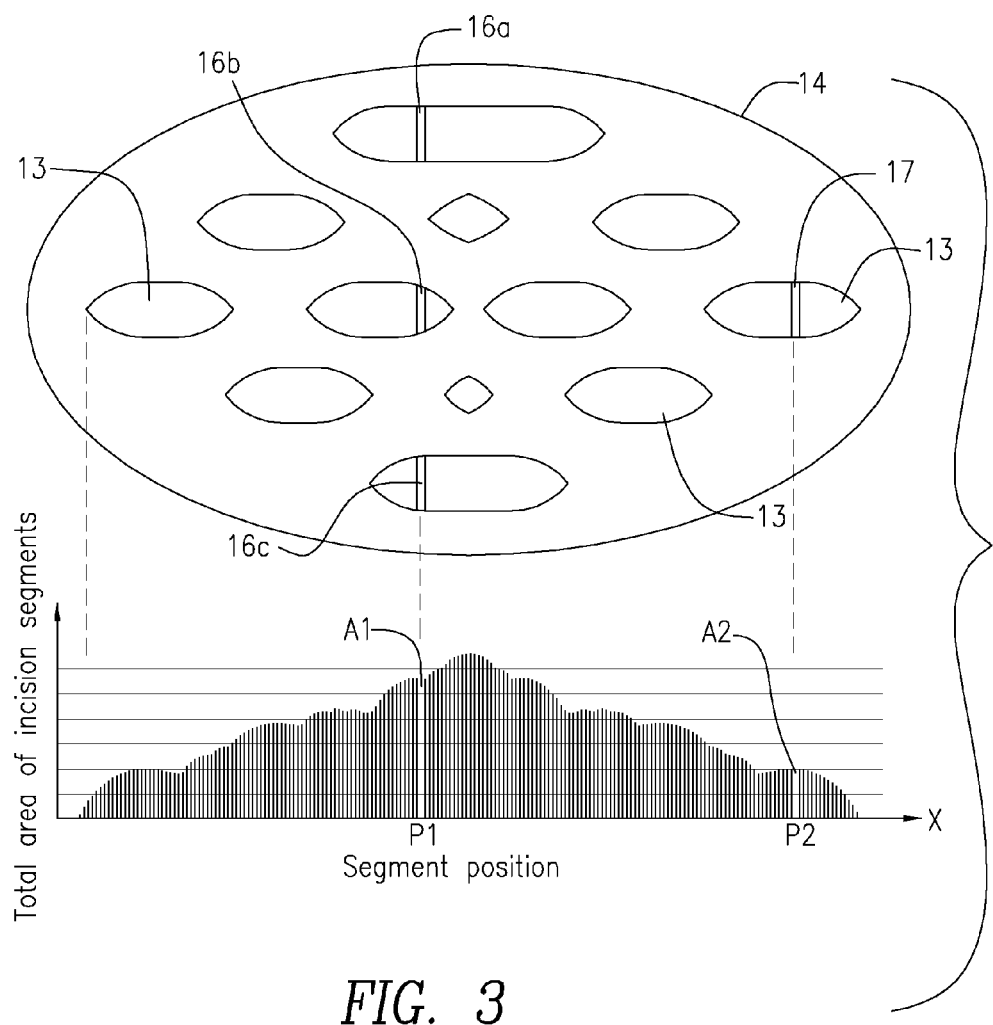
FIG. 3 illustrates a further embodiment according to the present invention in which a plurality of differently shaped incisions are arranged according to the "area rule" to collectively form an elliptical patch of skin to be treated.

FIG. 3 illustrates an embodiment in which an elliptical-shape skin patch 14 is collectively formed by a plurality of different navicular-like shaped incisions 13. Although the incisions 13 are different, the total area of incision segments still follow the "area rule" as shown in the area graphical representation in FIG. 3. This can be done by properly selecting the dimensions, shapes and locations of the incisions 13. Preferably, computer software can be written to assist in determining the size, shape and placement of the incisions 13 for a given skin patch 14 to be reduced. It is noted that exemplary total areas A1 and A2 at two positions P1, P2 and their associated incision segments 16a, 16b, 16c and 17 are illustrated in FIG. 3.

To make scar patterns less noticeable, the axes of the incisions 13 which extend across the two ends of the navicular shapes may be arranged more or less randomly unparallel to the axis "X" of the skin patch 14. In choosing the degree of variation from the axis "X", the area rule is preferably followed since the incisions 13 will be closed by moving skin on the lateral sides of the array substantially perpendicular to and toward the axis "X". For arrays that require curved axes, e.g., extremely long arrays relative to their width, the axis "X" can curve to conform to skin reduction requirements and lines of least skin tension. An example of a curved array that would not be considered long is an overall circular array with incision axes that form a curve to conform to wrinkle areas around the mouth or eyes.

Figure 4:
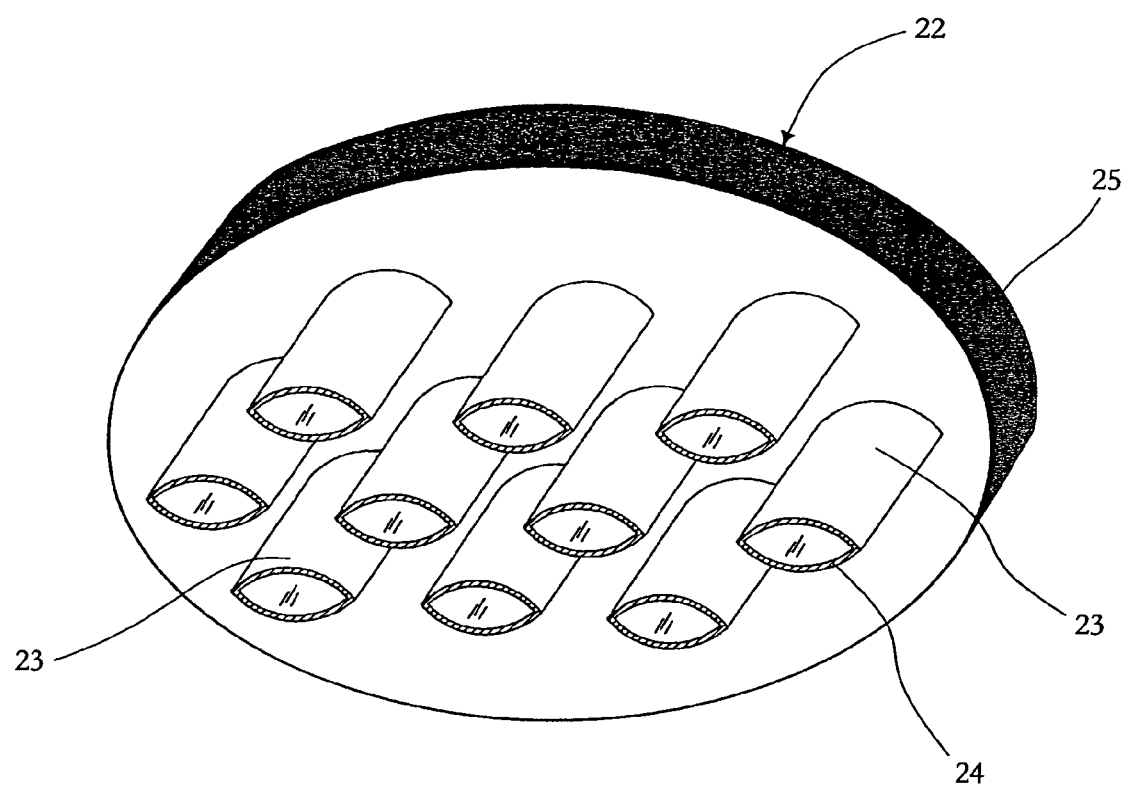
FIG. 4 illustrates an embodiment of a punch array according to the present invention.

The method of the present invention is preferably carried out by a punch array 22, which simultaneously makes the plurality of small incisions 13 that collectively form the skin patch 14 to be reduced. As illustrated in FIG. 4, a punch array 22 basically comprises an array of punches 23 collectively forming an operational region that matches the skin patch 14 to be reduced. An end of each punch 23 is provided with a cutting edge 24, and the other end is attached to a platform 25.

The cutting edge 24 of each punch 23 is sized and shaped to be suitable to make a corresponding incision 13 within the skin patch 14, and the punches 23 can be designed and positioned to meet the requirements of each specific type of skin reduction. For example, a scalp reduction might employ a two inch linear array of two rows of navicular punches using a flexible array support means to permit adaptation to the non-planer skin surfaces of the scalp, whereas a micro-face-lift surgical punch array might employ a configuration comprising a one-half inch elliptical array of five parallel rows of elliptical punches with different lumen sizes varying from one to three millimeters.

For large skin reductions, the method of the present invention can be implemented by using means to identify placement, shape and orientation of the incisions 13, such as a template or other marking means, and making the incisions 13 by hand with a scalpel or surgical punch. It is also contemplated to use machines to make excisions with lasers or other cutting means to perform an array skin reduction consistent with the method of the present invention.

Preferably, depth of the dermal layer is determined before applying the punch array 22 to make the incisions 13. Electronic or other means for determining dermal layer depth would make both machine and manual array incisions 13 more precise and safer by preventing incising delicate structures below the dermal layer. Also, incision position guides, e.g., rings in the shape of the incision 13 with adhesive for temporary attachment to the skin at predetermined incision sites, can be placed in an array to ensure proper placement of surgical punches or incisions to ensure precise reapplication of surgical punches or hand incisions if the initial incision did not cut completely through the dermal layer.

Figure 5:
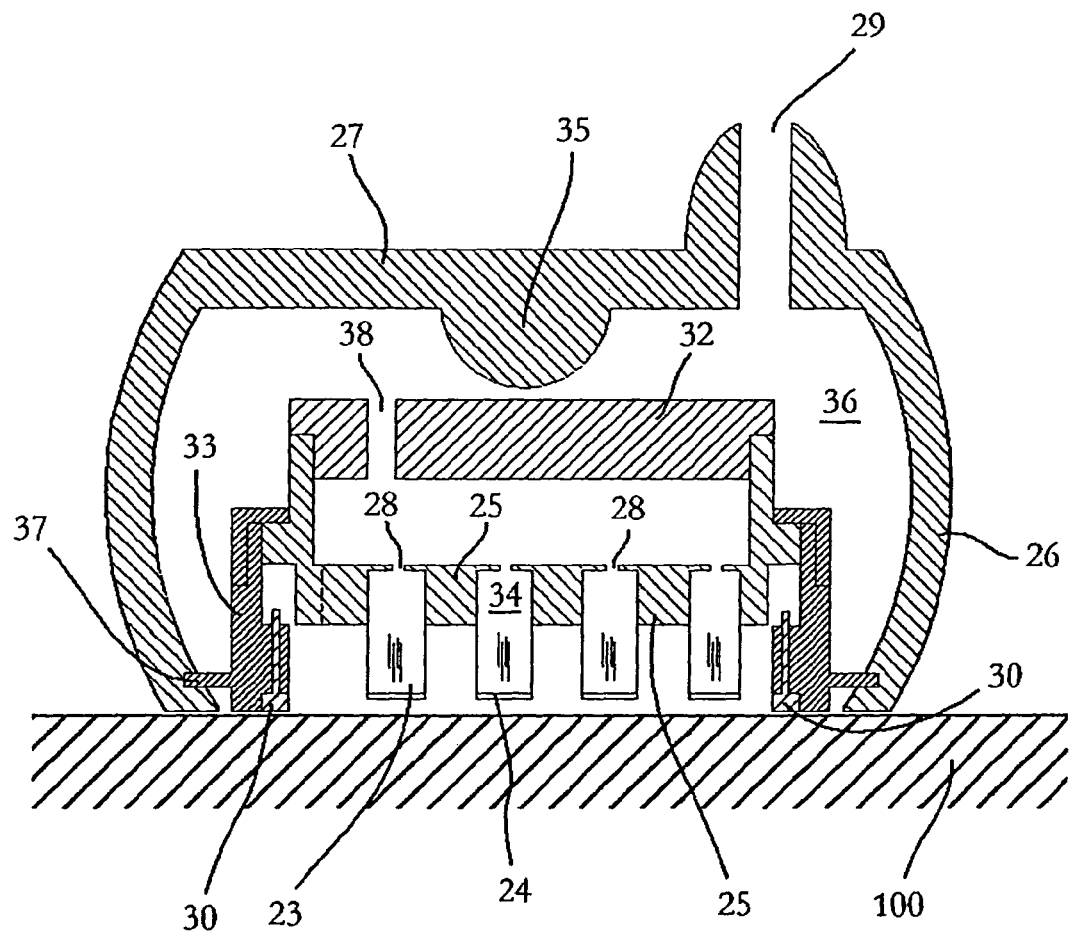
FIG. 5 is a sectional view illustrating an embodiment of apparatus according to the present invention which incorporates the punch array shown in FIG. 4.

An embodiment of surgical apparatus incorporating the punch array 22 according to the present invention is illustrated in FIG. 5. Although punches 23 can be replaced individually, preferably, the punches 23 can be changed by removing cylinder 33 from a flexible housing 26 by disengaging member 37 and replacing the used cylinder 33 with a new cylinder 33. Each punch 23 is a hollow tube with a lumen 34. A cutting edge 24 is provided at the free end of each punch 23, either being formed as an integral part of the punch 23 or is attached to the free end of the punch 23.

The platform 25 is held and accommodated inside the cylinder 33 and is slidable along an inner surface of the cylinder 33. The cylinder 33 is secured to the flexible drum-like housing 26 by the horizontal member 37.

The drum-like housing 26 has an open bottom, which allows the punches 23 to move therethrough toward the skin 100. The drum-like housing 26 has a top 27 having a hemispherical bulge 35 under its undersurface. The top 27 (or the whole housing 26) is preferably made of a resilient material such that when a force is applied on the top 27, the top 27 deforms and falls in. This brings the bulge 35 into contact with a cap 32 of the platform 25, and drives the cap 32 and therefore the platform 25 and the punches 23 to slide downward inside the cylinder 33 towards the skin 100, whereby cutting into the skin 100 for making the desired incisions 13. When the force is removed, the resilient top 27 returns to its initial state. Preferably, a biasing mechanism, such as a restoring spring (not shown), is also provided to return the platform 25 as well as the punches 23 back to their initial state as shown in FIG. 5 when the force applied on the top 27 is removed.

Preferably, a movement-limiting mechanism is provided to limit the sliding movement of platform 25 to a predetermined amount, whereby limiting the depth that the punches 23 cut into the skin 100. For example, as shown in FIG. 5, a stop ring 30 may be provided to limit the amount of the downward displacement of the platform 25. Preferably, the stop ring 30 is adjustably mounted to the cylinder 33 so as to adjust the amount of the movement of the platform as desired. Alternatively, the stop ring 30 can be replaced by one or more bolts mounted to the cylinder 33 to limit the vertical movement of the platform 25 to a desired amount, and the bolts are preferably adjustable vertically.

Figure 5A:
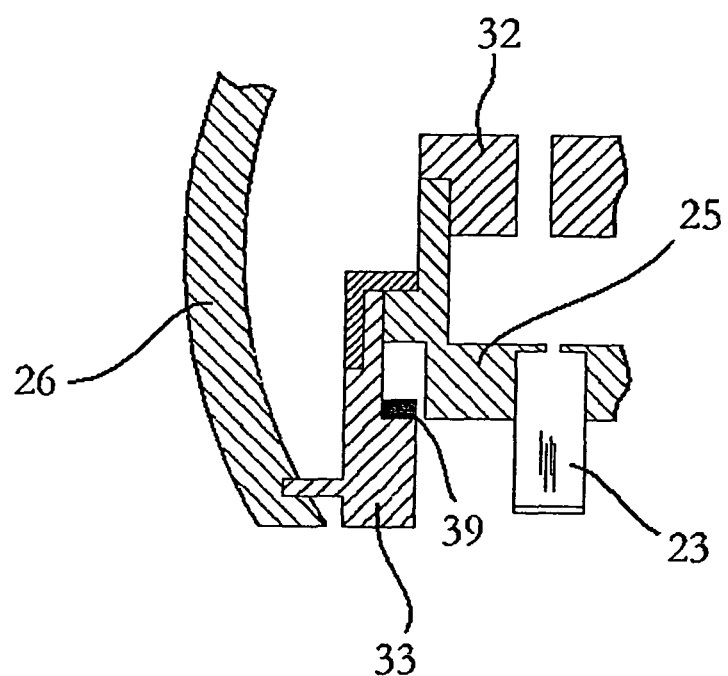
FIG. 5a partially illustrates an alternative embodiment of the apparatus in FIG. 5.

Alternatively, as illustrated In FIG. 5*a*, one or more washer-like rings 39 may be placed between an undersurface of the platform 25 and an inner shoulder of the cylinder 33 so as to limit the vertical movement of the platform 25 to a desired amount.

As shown in FIG. 5, a relief hole 28 is provided at the top of each punch 23 so that the air inside the lumen 34 can escape from the relief hole 28 when the punch 23 cuts into the skin 100, whereby avoiding forming a pressure inside the lumen 34 above the skin plug that enters the lumen 34.

Preferably, suction is applied to the lumen 34 through the relief hole 28 to hold the skin plug inside the lumen 34 so it can be removed together with the punch 23 when the punch 23 leaves the skin, or to help detaching the skin plug from the subdermal tissue. The suction can be applied from a vent 29 provided on the top 27 of the housing 26, and communicates with each punch 23 via a port 38 provided on the cap 32 of the platform 25 and each relief hole 28. Besides, as an alternative to applying an external force on the top 27 to drive the cap 32, by reducing pressure in housing 26, outside pressure deforms housing 26 and hemispherical bulge 35 presses against cap 32, thereby driving the cutting array of punches 23 into the skin 100.

Figure 6:
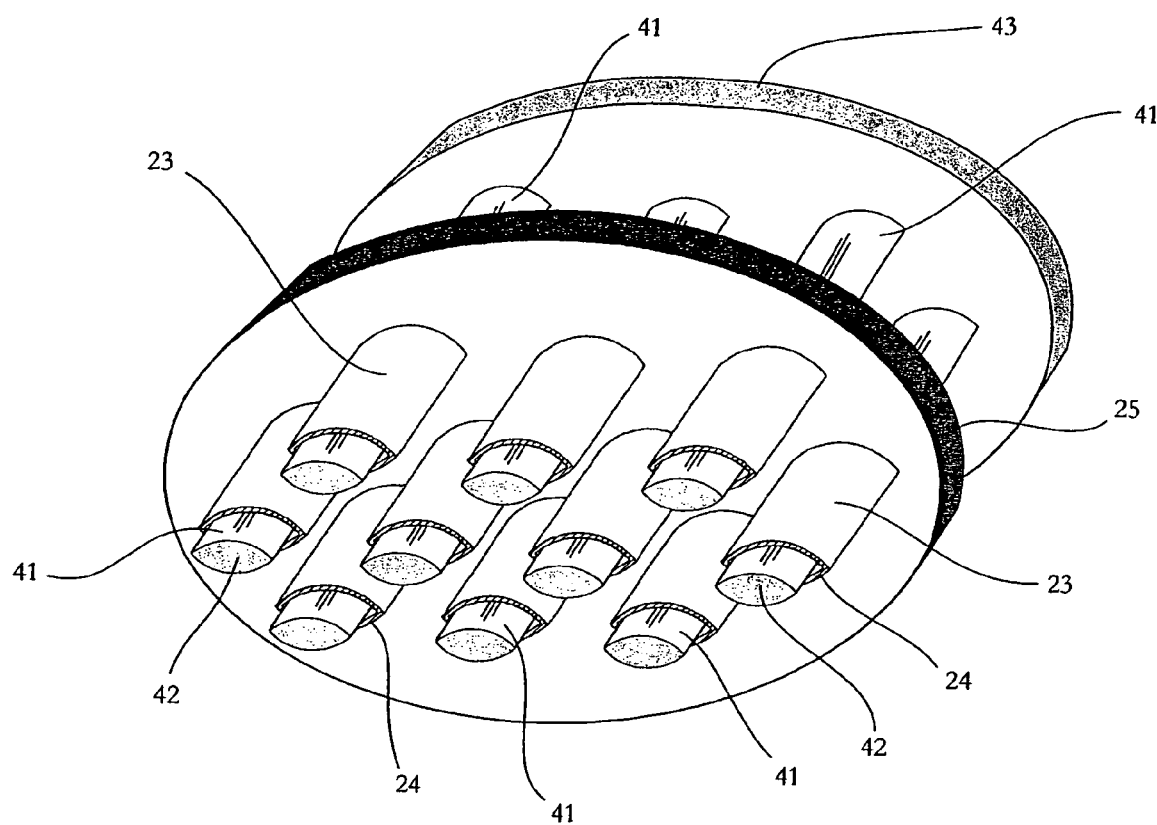
FIG. 6 illustrates another embodiment of a punch array according to the present invention.

Alternatively, as illustrated in FIG. 6, an in-line array of gripping rods 41 are arranged to pass through their counterpart surgical punches 23. The leading surfaces of the gripping rods 41 are coated with a skin adhesive 42 that is intended to contact the skin 100 such that the incised skin plugs are gripped by the adhesive 42 and are forcibly removed as the array of rods 41 are removed after incision.

Figure 7:
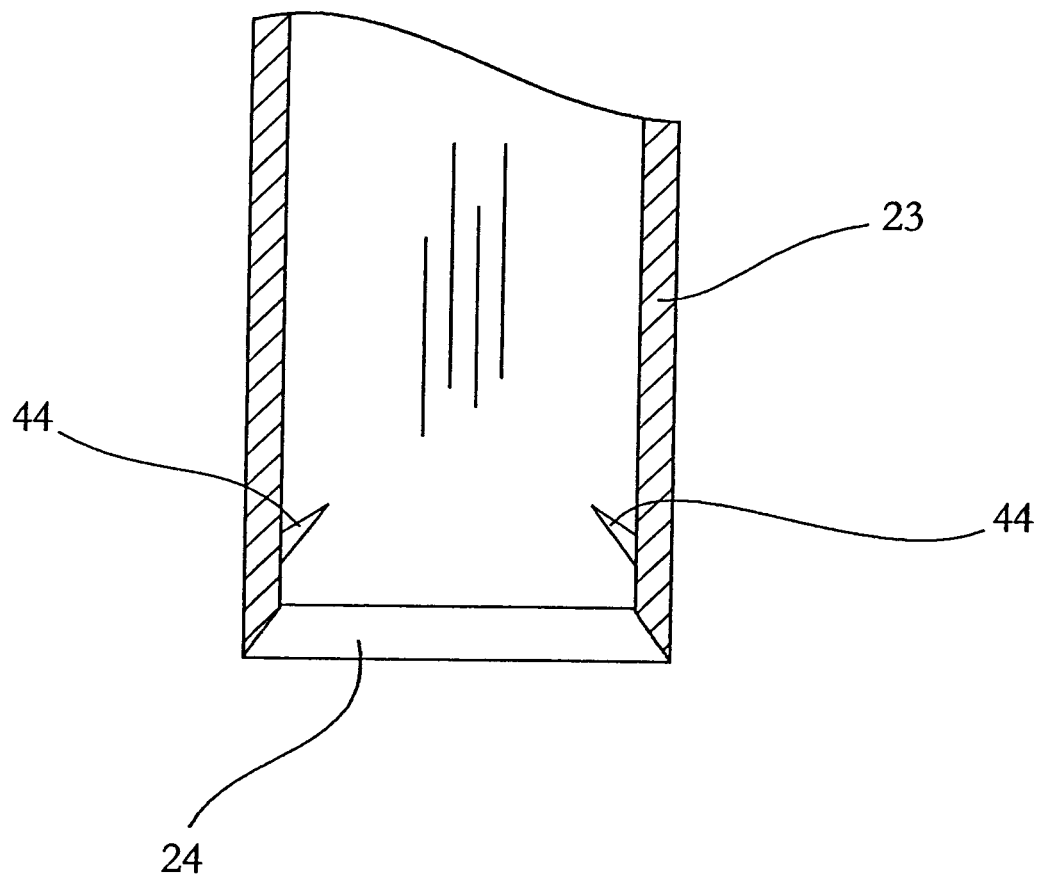
FIG. 7 illustrates an embodiment of the punch.

Alternative or in addition to the adhesive rods 41, one or more upward barbs 44 are provided on the inner walls of the surgical punches 23, as shown in FIG. 7. The barbs 44 secure the skin plugs within the surgical punches 23 and forcibly remove the plugs as the surgical array is removed. Alternatively, a spear-like barb or equivalent (not shown) can be attached to the end of rods 41 to mechanically engage and withdraw skin plugs formed by incisions of punches 23.

The incision operation incorporating the teaching of the present invention is described further below. When the array of punches 23 are applied to the skin 100, multiple precise incisions 13 are made through the dermal layer. If the punches 23 have lumens 34 measuring a few millimeters, the skin plugs created by the punches 23 will be withdrawn with the array of punches 23. If the lumens 34 are larger and barbs 44 or adhesive rods 41 are not employed to hold the skin plugs within the punches 23 as they are withdrawn, the in situ plugs can be removed surgically or by applying suction to the array of punches 23 through the relief holes 28 when the incisions are being made, such that incised plugs of skin are drawn into and retained in the lumens 34 of the surgical punches 23 as they are removed. If incised plugs still remain attached to the sub-dermal tissue, other means for removal should be employed, such as with a pin or tweezers and possibly scissors to cut the plugs free from the fat layer. In addition, means for reciprocating the surgical punches 23 or punch array 22 to enhance its cutting action can be attached to means (e.g., the housing 26) used by the surgeon to hold the surgical cutting device during its use.

In a typical application, after the patch 14 of skin to be reduced is selected, the skin is cleansed and anesthetized, e.g., with two percent lidocaine with epinephrine. In determining how to orient the surgical punch array 22, the lines of least skin tension should be identified. For example, on the arm these lines run perpendicular to the long axis of the arm. The axes of surgical punches will normally be oriented parallel to the lines of least skin tension. To apply the surgical punch array 22 to make an array of incisions 13, skin surrounding the incision site (i.e., the selected patch) can be stretched with the thumb and index finger perpendicular to the lines of least skin tension, e.g., along the long axis of the arm. Once the punch array 22 has penetrated the dermis and begins to penetrate the subcutaneous fat layer, penetration should be stopped and the array removed. When using a surgical punch array 22 on areas where the skin is thin, such as the face, neck or distal extremities, it is possible to damage arteries, nerves and veins below the skin. Most surgeons can identify when a hand-held punch penetrates the dermis because a "give" can be felt. With a surgical punch array 22, feeling a "give" might not be possible. Therefore, methods for determining skin thickness and means for presetting the depth of penetration are preferably employed when using a surgical punch array 22 on areas like the face, neck or distal extremities.

Upon withdrawal of the surgical punch array 22 from the skin 100 there may be a tendency of the cut tissue to remain in place. Suction forcing the tissue into the surgical punch 23 is recommended. Alternatively or in addition to the use of suction, an upward pointing barb or hook 44 can be situated inside the punch 23 to engage and retain the tissue. It is further recommended that relief holes 28 be placed in the upper portion of each surgical punch 23 to allow air trapped in the punch 23 during incision to escape. When suction is used, these same relief holes 28 provide a passage through which the suction source can communicate with the tissue plugs to draw them into the surgical punch array 22 for extraction. In the event plugs of tissue are not removed as the surgical incision array 22 is removed, as would be expected for large surgical incision arrays, these plugs of tissue should be removed with appropriate instruments while being careful to prevent tissue from dropping down and lodging under the dermis layer. Scissors can be used to cut the tissue below the dermis to free it from subcutaneous tissues. After the tissue plugs are removed, array incision dimensions in the direction of the initial skin stretching will reduce as the skin is released and relaxes to its original state. This process results in a partial closing of the wounds. For larger surgical punch wounds, the wound is closed with an appropriate number of sutures using, e.g., 5-0 or 6-0 nylon. The suture generally creates good hemostasis, and antibiotic ointment and a bandage can be applied. For smaller wounds, a cyanoacrylate tissue adhesive can be applied instead of sutures. Cyanoacrylate adhesive forms a strong bond across opposed wound edges, allowing normal healing to occur below. These adhesives are marketed to replace sutures that are 5-0 or smaller in diameter for incisional and other repair. This adhesive provides a flexible water-resistant protective coating, eliminates the need for suture removal, and, when very small surgical punches 23 are used, adhesive closure might be the only practical closure method. The long-term cosmetic outcome with cyanoacrylate adhesives is comparable to that of traditional methods of repair. Smaller incisions 13 can often be cleansed with an antibacterial compound and flushed with sterile saline solution before closure. The edges of the wound must be approximated manually and evenly. If there is uncertainty about whether this can be done, the wound should probably be sutured instead. Once the edges have been approximated, adhesive is applied to the opposed wound edges. After applying adhesive across the wound edges and holding the edges together for at least thirty seconds before releasing, more adhesive should be applied in an oval pattern around the wound to encompass a greater surface area on the skin. This adds greater strength to the wound closure. At least three layers should be applied to ensure optimal strength and no added coverings are needed. The first layer of adhesive reaches maximal strength within two and one-half minutes. The adhesive will spontaneously peel off in five to ten days. Use of the apparatus of the present invention can be repeated, e.g., on an outpatient basis until the desired amount and direction of skin reduction is achieved. If multiple visits are employed, the results of previous procedures can be adjusted with each new visit by choosing the precise size and placement of subsequent punch array applications to perfect the skin reduction.

Figure 8:
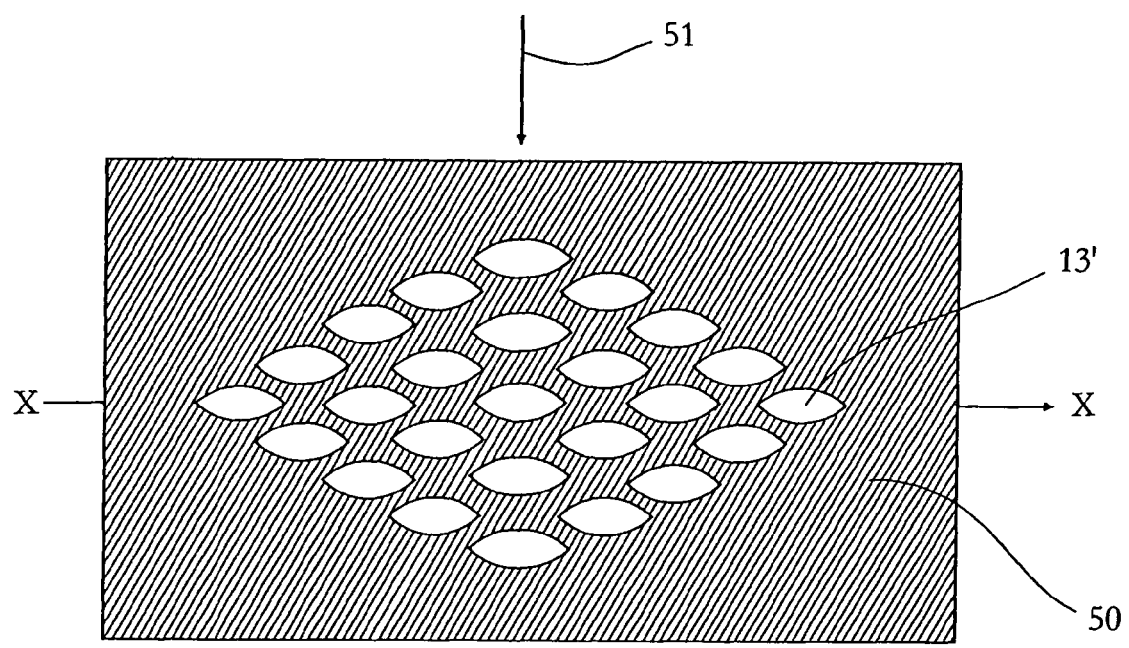
FIG. 8 illustrates an embodiment in which the skin is treated using a laser.

As an alternative to mechanical excisions by, e.g., the array of punches, the skin reduction may be realized by laser treatment. Preferably, as illustrated in FIG. 8, a mask 50 is provided to cover the patch of skin to be reduced by a laser 51. The mask 50, which is made of a material capable of preventing the laser 51 from passing through, has a plurality of holes 13' that allow the laser beam 51 to pass through. Each hole 13' exposes a region of skin to the laser 51 to be reduced by the laser 51. The laser 51 vaporizes the regions of skin exposed by the holes 13' on the mask 50. The duration of laser exposure should be sufficient to vaporize the dermal layer, but insufficient to vaporize sub-dermal tissue.

Preferably, the holes 13' are dimensioned and arranged to follow the "area rule", i.e., a total area of all removed or treated skin segments taken in a direction perpendicular to an axis "X" of the patch with a predetermined width along the axis "X" varying gradually along said axis "X". In a preferred embodiment, the holes 13' are navicular in shape.

Preferably, laser 51 may comprise one or more wide area beams each covering one or more of the holes 13'. Because of the protection of the mark 50, only the regions defined by the holes 13' are treated by the laser beams.

Some or all of the wide area beams may stay statically above the relevant hole or holes 13', or may move around so that one wide area beam may treat different regions one after another.

As an alternative, the laser 51 may comprise a single narrow beam that moves from one region to another in a predetermined pattern that is equivalent to the pattern of regions of skin exposed by the laser mask 50 described above. The beam can be turned off when it is moving, and turned on when it is moved to a desired position for treating a targeted region. Thus, the single beam may treat all the skin regions. In addition, the mask 50 may be omitted if the narrow beam has a cross-sectional shape that matches each region.

In another embodiment, instead of treating navicular or elliptical regions of skin, the laser 51 may perform narrow line incisions, which may be measured in millimeters and smaller. In particular, the laser 51 may make multiple, substantially parallel narrow line excisions of same or different lengths, which collectively form the patch of skin to be treated. Compared to treating the patch with a single large incision, multiple small excisions reduce the appearance of scarring even without following the "area rule". In addition, with narrow line excisions, the "dog ear" effect experienced with wider excisions would not be significant.

Preferably, the beginning and end areas of the line excision array may follow the gradual transition "area rule", while the substantially parallel and continuous portion of the excision array between the beginning and end areas would experience no combined excision area transition. Preferably, the narrow line excisions are spaced apart sufficiently.

When applied to excising tissue, it is necessary to control the depth as well as the pattern of laser cutting. Although Fitzpatrick scale of skin types can be used for a given laser to estimate penetration levels for different shades of skin color, an alternative would be to use the equivalent of an ultrasound scanner designed to measure skin thickness and subsurface structures. It is likely that cut depth testing with a scanning ultrasound device, such as those used to analyze decubitus ulcers, would be useful in determining the settings for excising tissue with a motion controlled narrow beam laser as well as testing the cut depth after each exposure of wide area lasers that can be used multiple times to excise tissue on all or part of a mask described above.

It is noted that another embodiment includes the use of an adhesive on the mask 50. More specifically, the mask 50 may be adhered to the skin before the laser or other treatment described above by an adhesive on the mask itself, on the area of skin to be treated, or by using a two sided adhesive film, one side of which sticks to the mask, and the other side of which adheres to the skin. Adhering the mask to the skin ensures that the mask will not move from its original placement position during the procedure. The skin may preferably be stretched first, and the adherence of the mask to the skin during the procedure will keep the skin from unstretching during such procedure. Alternatively, very minor tacks or points bent downward and outwardly may pierce only the top layer(s) of the skin and grip it to hold it in the stretched position. After the procedure, the skin will then un-stretch.

Alternatively, any type of tacky material or mechanical device may be used to hold the mask against the stretched or unstretched skin during the procedure. The mask may even be taped over, or secured at its edges with clips or other mechanisms that adhere to or slightly pierce the skin.

Although the foregoing has described the preferred embodiments of the present invention, it shall be understood that, without departing from the spirit of the present invention, numerous variations, adaptations and modifications are available to a person with ordinary skill in the art. For example, instead of a simultaneous operation by the punch array 22, the plurality of incisions 13 can be made individually one by one by a small punch. Additionally, the tissue may be removed by other techniques, e.g., by vaporizing the tissue even though the incisions are made by a punch or other means. Moreover, the removal or treatment of the regions of skin may be carried out by other proper methods other than incisions or laser treatment. Therefore, the scope of the present invention is intended to be solely defined by the accompanying claims.

The invention claimed is:

1. A method for reducing skin, the method comprising:
    identifying a patch of skin to be treated;
    covering the patch of skin with a mask comprising a masking panel and a navicular or elliptical shaped array of mask openings in the masking panel, each of the openings having a navicular or elliptical shape, the array of mask openings comprising first and second ends, first and second sides, a longitudinal axis, a first length measured between the first and second ends of the array, and a first width measured between the first and second sides of the array, the first length extending in a same direction as the longitudinal axis and being greater than the first width, each of the mask openings comprising first and second ends, first and second sides, a long axis, a second length measured between the first and second ends of the opening, and a second width measured between the first and second sides of the opening, the second length extending in a same direction as the long axis and being greater than the second width, the long axis of each of the openings being parallel with the longitudinal axis of the array; and removing portions of skin aligned with the mask openings to reduce the area of the patch of skin.

2. The method of claim 1 wherein the portions of skin removed through the mask openings define an array of open incisions having a cumulative width that varies as a function of position along a first axis of the patch of skin.

3. The method of claim 2 further comprising closing the open incisions.

4. The method of claim 1 wherein the removing of the portions of skin is performed one portion at a time.

5. The method of claim 1 wherein the removing of the portions of skin is performed contemporaneously.

6. The method of claim 1 further comprising stretching said patch of skin into a stretched position prior to the covering of the patch of skin with the mask.

7. The method of claim 6 wherein said mask retains said patch of skin in the stretched position.

8. The method of claim 1 wherein said mask is larger than said patch of skin.

9. The method of claim 1 further comprising holding said mask in place on said patch of skin with an adhesive.

10. The method of claim 1 wherein said mask further comprises an adhesive to hold said mask in place on said patch of skin.

11. The method of claim 1 further comprising applying an adhesive to said patch of skin before the covering with the mask.

12. The method of claim 1 wherein said mask further comprises a two-sided adhesive film for holding said mask in place on said patch of skin.

13. The method of claim 1 wherein the mask further comprises tacks or points and further comprising maintaining the patch of skin in the stretched position using tacks or points of the mask.

14. The method of claim 1 wherein said mask is held in place by adhesive tape placed partially over mask and on said skin proximate to said mask.

15. A mask for treating a patch of skin, the mask comprising:
a masking panel; and
a navicular or elliptical shaped array of mask openings in the masking panel, each of the openings having a navicular or elliptical shape;
wherein the array of mask openings comprises first and second ends, first and second sides, a longitudinal axis, a first length measured between the first and second ends of the array, and a first width measured between the first and second sides of the array, the first length extending in a same direction as the longitudinal axis and being greater than the first width;
wherein each of the mask openings comprises first and second ends, first and second sides, a long axis, a second length measured between the first and second ends of the opening, and a second width measured between the first and second sides of the opening, the second length extending in a same direction as the long axis and being greater than the second width, the long axis of each of the openings being parallel with the longitudinal axis of the array.

16. The mask of claim 15 wherein the array of mask openings has a cumulative width that varies as a function of position along the longitudinal axis thereof.

17. The mask of claim 15 wherein the second width of each of the mask openings varies continuously as a function of position along the long axis thereof.

18. The mask of claim 15 further comprising an adhesive disposed on a side of the masking panel faces for hold the mask against the patch of skin.

19. The mask of claim 15 further comprising an adhesive strip disposed on a side of the masking panel faces for hold the mask against the patch of skin.

20. A method for reducing skin, the method comprising:
identifying a patch of skin to be treated, the patch of skin having a first axis;
adhering a mask to the patch of skin, the mask comprising a masking panel and a navicular or elliptical shaped array of mask openings in the masking panel, each of the openings having a navicular or elliptical shape, the array of mask openings comprising first and second ends, first and second sides, a longitudinal axis, a first length measured between the first and second ends of the array, and a first width measured between the first and second sides of the array, the first length extending in a same direction as the longitudinal axis and being greater than the first width, each of the mask openings comprising first and second ends, first and second sides, a long axis, a second length measured between the first and second ends of the opening, and a second width measured between the first and second sides of the opening, the second length extending in a same direction as the long axis and being greater than the second width, the long axis of each of the openings being parallel with the longitudinal axis of the array; and
removing portions of skin aligned with the mask openings to reduce the area of the patch of skin.

21. The method of claim 20 wherein the portions of skin removed through the mask openings define an array of open incisions having a cumulative width that varies as a function of position along the first axis of the patch of skin.

22. The method of claim 20 further comprising closing the open incisions.

23. The method of claim 20 wherein the removing of the portions of skin is performed one portion at a time.

24. The method of claim 20 wherein the removing of the portions of skin is performed contemporaneously.

25. The method of claim 20 wherein said removing is performed using a device separate from said mask.

26. The method of claim 20 wherein said step of removing is performed using a laser.

27. The method of claim 20 wherein said adhering includes taping over said mask.

28. The method of claim 20 further comprising first stretching the patch of skin prior to attaching said mask.

29. The method of claim 28 further comprising removing adhesive used in said adhering step from said skin after removing said mask from said patch of skin.

30. The method of claim 20 further comprising deforming said patch of skin.

31. The method of claim 30 comprising deforming said patch of skin such that said mask is larger than said patch of skin.

32. The method of claim 30 wherein said mask is held in place on said patch of skin by an adhesive.

33. The method of claim 32 wherein said adhesive is provided on said mask.

34. The method of claim 32 wherein said adhesive is applied to said patch.

35. The method of claim 32 wherein said mask further comprises a two-sided adhesive film for holding said mask in place on said patch of skin.

36. The method of claim 20 wherein said mask further comprises tacks or points and wherein the patch of skin is maintained in a stretched position by tacks or points of the mask.

37. The method of claim 20 wherein said mask is held in place by adhesive tape placed partially over said mask and on skin proximate to said mask.

\* \* \* \* \*